US012797190B2

(12) United States Patent
Braido et al.

(10) Patent No.: US 12,797,190 B2
(45) Date of Patent: Nov. 17, 2026

(54) VALVE ASSEMBLY FOR CRIMP PROFILE

(71) Applicant: St. Jude Medical, Cardiology Division, Inc., St. Paul, MN (US)

(72) Inventors: Peter Nicholas Braido, Wyoming, MN (US); Daniel Coyle, Apple Valley, MN (US); Mary Johnson, St. Paul, MN (US); Julia Ann Schraut, Shoreview, MN (US); Ryan Buesseler, Delano, MN (US); Jacob John Daly, Blaine, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 341 days.

(21) Appl. No.: 18/640,680

(22) Filed: Apr. 19, 2024

(65) Prior Publication Data

US 2024/0261093 A1 Aug. 8, 2024

Related U.S. Application Data

(60) Continuation of application No. 18/050,266, filed on Oct. 27, 2022, now Pat. No. 12,076,239, which is a (Continued)

(51) Int. Cl.
*A61F 2/95* (2013.01)
*A61F 2/24* (2006.01)
*A61F 2/90* (2013.01)

(52) U.S. Cl.
CPC .......... *A61F 2/2418* (2013.01); *A61F 2/2415* (2013.01); *A61F 2/90* (2013.01);
(Continued)

(58) Field of Classification Search
CPC ................. B23Q 3/00; A61F 2/24; A61F 2/06
See application file for complete search history.

(56) References Cited

U.S. PATENT DOCUMENTS 3,657,744 A 4/1972 Ersek
4,275,469 A 6/1981 Gabbay
(Continued)

FOREIGN PATENT DOCUMENTS

DE 19857887 B4 5/2005
DE 10121210 B4 11/2005
(Continued)

OTHER PUBLICATIONS

"Transluminal Implantation of Artificial Heart Valves", Andersen, H. R., et al., European Heart Journal, vol. 13, No. 5, May 1992, pp. 704-708.

(Continued)

*Primary Examiner* — Lee D Wilson
(74) *Attorney, Agent, or Firm* — SLEMAN & LUND LLP

(57) ABSTRACT

A method of assembling a prosthetic heart valve includes providing a collapsible and expandable stent having an annulus section and an aortic section. The annulus section has a first diameter in a relaxed condition and a second diameter less than the first diameter in a collapsed condition. A constraint is applied to the stent to constrain the annulus section to a predetermined diameter between the first and second diameters. Applying a cuff and/or a plurality of leaflets to the stent in the constrained condition enables less material to be used. The resultant prosthetic valve is therefore able to be collapsed to a smaller diameter for introduction into a patient.

20 Claims, 7 Drawing Sheets

Related U.S. Application Data continuation of application No. 16/297,060, filed on Mar. 8, 2019, now Pat. No. 11,660,186, which is a division of application No. 14/882,669, filed on Oct. 14, 2015, now Pat. No. 10,470,880, which is a continuation of application No. 13/788,696, filed on Mar. 7, 2013, now Pat. No. 9,241,791.

(60) Provisional application No. 61/666,174, filed on Jun. 29, 2012.

(52) U.S. Cl.
CPC .............. *A61F 2/95* (2013.01); *A61F 2/2409* (2013.01); *A61F 2/2436* (2013.01); *A61F 2002/9505* (2013.01); *A61F 2002/9511* (2013.01); *A61F 2220/0075* (2013.01); *Y10T 29/49405* (2015.01); *Y10T 29/49925* (2015.01); *Y10T 29/49936* (2015.01); *Y10T 29/4994* (2015.01)

(56) References Cited

U.S. PATENT DOCUMENTS

| | | | | |
|---|---|---|---|---|
| 4,491,986 | A | 1/1985 | Gabbay | |
| 4,759,758 | A | 7/1988 | Gabbay | |
| 4,878,906 | A | 11/1989 | Lindemann | |
| 4,922,905 | A | 5/1990 | Strecker | |
| 4,994,077 | A | 2/1991 | Dobben | |
| 5,411,552 | A | 5/1995 | Andersen | |
| 5,480,423 | A | 1/1996 | Ravenscroft | |
| 5,843,158 | A | 12/1998 | Lenker | |
| 5,843,167 | A | 12/1998 | Dwyer | |
| 5,855,601 | A | 1/1999 | Bessler | |
| 5,935,163 | A | 8/1999 | Gabbay | |
| 5,961,549 | A | 10/1999 | Nguyen | |
| 6,042,606 | A * | 3/2000 | Frantzen | A61F 2/915 623/1.3 |
| 6,077,297 | A | 6/2000 | Robinson | |
| 6,083,257 | A | 7/2000 | Taylor | |
| 6,090,140 | A | 7/2000 | Gabbay | |
| 6,214,036 | B1 | 4/2001 | Letendre | |
| 6,264,691 | B1 | 7/2001 | Gabbay | |
| 6,267,783 | B1 | 7/2001 | Letendre | |
| 6,368,348 | B1 | 4/2002 | Gabbay | |
| 6,419,695 | B1 | 7/2002 | Gabbay | |
| 6,468,660 | B2 | 10/2002 | Ogle | |
| 6,488,702 | B1 | 12/2002 | Besselink | |
| 6,517,576 | B2 | 2/2003 | Gabbay | |
| 6,533,810 | B2 * | 3/2003 | Hankh | A61F 2/90 623/1.3 |
| 6,558,414 | B2 | 5/2003 | Layne | |
| 6,582,464 | B2 | 6/2003 | Gabbay | |
| 6,610,088 | B1 | 8/2003 | Gabbay | |
| 6,623,518 | B2 | 9/2003 | Thompson | |
| 6,685,625 | B2 | 2/2004 | Gabbay | |
| 6,719,789 | B2 | 4/2004 | Cox | |
| 6,730,118 | B2 | 5/2004 | Spenser | |
| 6,783,556 | B1 | 8/2004 | Gabbay | |
| 6,790,230 | B2 | 9/2004 | Beyersdorf | |
| 6,814,746 | B2 | 11/2004 | Thompson | |
| 6,830,584 | B1 | 12/2004 | Seguin | |
| 6,869,444 | B2 | 3/2005 | Gabbay | |
| 6,893,460 | B2 | 5/2005 | Spenser | |
| 6,908,481 | B2 | 6/2005 | Cribier | |
| 6,929,659 | B2 | 8/2005 | Pinchuk | |
| 7,018,406 | B2 | 3/2006 | Seguin | |
| 7,022,132 | B2 | 4/2006 | Kocur | |
| 7,025,780 | B2 | 4/2006 | Gabbay | |
| 7,137,184 | B2 | 11/2006 | Schreck | |
| 7,160,322 | B2 | 1/2007 | Gabbay | |
| 7,247,167 | B2 | 7/2007 | Gabbay | |
| 7,267,686 | B2 | 9/2007 | DiMatteo | |
| 7,311,730 | B2 | 12/2007 | Gabbay | |
| 7,329,278 | B2 | 2/2008 | Seguin | |
| 7,374,573 | B2 | 5/2008 | Gabbay | |
| 7,381,218 | B2 | 6/2008 | Schreck | |
| 7,452,371 | B2 | 11/2008 | Pavcnik | |
| 7,510,572 | B2 | 3/2009 | Gabbay | |
| 7,524,331 | B2 | 4/2009 | Birdsall | |
| RE40,816 | E | 6/2009 | Taylor | |
| 7,585,321 | B2 | 9/2009 | Cribier | |
| 7,682,390 | B2 | 3/2010 | Seguin | |
| 7,731,742 | B2 | 6/2010 | Schlick | |
| 7,803,185 | B2 | 9/2010 | Gabbay | |
| 7,846,203 | B2 | 12/2010 | Cribier | |
| 7,846,204 | B2 | 12/2010 | Letac | |
| 7,914,569 | B2 | 3/2011 | Nguyen | |
| D648,854 | S | 11/2011 | Braido | |
| D652,926 | S | 1/2012 | Braido | |
| D652,927 | S | 1/2012 | Braido | |
| D653,341 | S | 1/2012 | Braido | |
| D653,342 | S | 1/2012 | Braido | |
| D653,343 | S | 1/2012 | Ness | |
| D654,169 | S | 2/2012 | Braido | |
| D654,170 | S | 2/2012 | Braido | |
| D660,432 | S | 5/2012 | Braido | |
| D660,433 | S | 5/2012 | Braido | |
| D660,967 | S | 5/2012 | Braido | |
| 8,414,644 | B2 | 4/2013 | Quadri | |
| 8,926,686 | B2 | 1/2015 | King | |
| 9,241,791 | B2 | 1/2016 | Braido | |
| 11,660,186 | B2 | 5/2023 | Braido | |
| 2002/0036220 | A1 | 3/2002 | Gabbay | |
| 2003/0023303 | A1 | 1/2003 | Palmaz | |
| 2003/0050694 | A1 | 3/2003 | Yang | |
| 2003/0130726 | A1 | 7/2003 | Thorpe | |
| 2004/0049262 | A1 | 3/2004 | Obermiller | |
| 2004/0093075 | A1 | 5/2004 | Kuehne | |
| 2004/0210304 | A1 | 10/2004 | Seguin | |
| 2005/0096726 | A1 | 5/2005 | Sequin | |
| 2005/0137695 | A1 | 6/2005 | Salahieh | |
| 2005/0137697 | A1 | 6/2005 | Salahieh | |
| 2005/0256566 | A1 | 11/2005 | Gabbay | |
| 2006/0008497 | A1 | 1/2006 | Gabbay | |
| 2006/0074484 | A1 | 4/2006 | Huber | |
| 2006/0122692 | A1 | 6/2006 | Gilad | |
| 2006/0149360 | A1 | 7/2006 | Schwammenthal | |
| 2006/0173532 | A1 | 8/2006 | Flagle | |
| 2006/0178740 | A1 | 8/2006 | Stacchino | |
| 2006/0206202 | A1 | 9/2006 | Bonhoeffer | |
| 2006/0241744 | A1 | 10/2006 | Beith | |
| 2006/0241745 | A1 | 10/2006 | Solem | |
| 2006/0259120 | A1 | 11/2006 | Vongphakdy | |
| 2006/0259137 | A1 | 11/2006 | Artof | |
| 2006/0265056 | A1 * | 11/2006 | Nguyen | A61F 2/2418 623/2.18 |
| 2006/0276813 | A1 | 12/2006 | Greenberg | |
| 2007/0010876 | A1 | 1/2007 | Salahieh | |
| 2007/0027534 | A1 | 2/2007 | Bergheim | |
| 2007/0043435 | A1 | 2/2007 | Seguin | |
| 2007/0055358 | A1 | 3/2007 | Krolik | |
| 2007/0067029 | A1 | 3/2007 | Gabbay | |
| 2007/0093890 | A1 | 4/2007 | Eliasen | |
| 2007/0100435 | A1 | 5/2007 | Case | |
| 2007/0118210 | A1 | 5/2007 | Pinchuk | |
| 2007/0213813 | A1 | 9/2007 | Von Segesser | |
| 2007/0233228 | A1 | 10/2007 | Eberhardt | |
| 2007/0244545 | A1 | 10/2007 | Birdsall | |
| 2007/0244552 | A1 | 10/2007 | Salahieh | |
| 2007/0288087 | A1 | 12/2007 | Fearnot | |
| 2008/0021552 | A1 | 1/2008 | Gabbay | |
| 2008/0039934 | A1 | 2/2008 | Styrc | |
| 2008/0071369 | A1 | 3/2008 | Tuval | |
| 2008/0082164 | A1 | 4/2008 | Friedman | |
| 2008/0097595 | A1 | 4/2008 | Gabbay | |
| 2008/0114452 | A1 | 5/2008 | Gabbay | |
| 2008/0125853 | A1 | 5/2008 | Bailey | |
| 2008/0140189 | A1 | 6/2008 | Nguyen | |
| 2008/0147179 | A1 | 6/2008 | Cai | |
| 2008/0147183 | A1 | 6/2008 | Styrc | |
| 2008/0154355 | A1 | 6/2008 | Benichou | |
| 2008/0154356 | A1 | 6/2008 | Obermiller | |

(56) References Cited

U.S. PATENT DOCUMENTS

| | | | |
|---|---|---|---|
| 2008/0228264 | A1 | 9/2008 | Li |
| 2008/0243245 | A1 | 10/2008 | Thambar |
| 2008/0255662 | A1 | 10/2008 | Stacchino |
| 2008/0262602 | A1 | 10/2008 | Wilk |
| 2008/0269879 | A1 | 10/2008 | Sathe |
| 2008/0319526 | A1 | 12/2008 | Hill |
| 2009/0112309 | A1 | 4/2009 | Jaramillo |
| 2009/0138079 | A1 | 5/2009 | Tuval |
| 2009/0157175 | A1 | 6/2009 | Benichou |
| 2010/0004740 | A1 | 1/2010 | Seguin |
| 2010/0036484 | A1 | 2/2010 | Hariton |
| 2010/0049293 | A1 | 2/2010 | Zukowski |
| 2010/0049306 | A1 | 2/2010 | House |
| 2010/0087907 | A1 | 4/2010 | Lattouf |
| 2010/0131055 | A1 | 5/2010 | Case |
| 2010/0168778 | A1 | 7/2010 | Braido |
| 2010/0168839 | A1 | 7/2010 | Braido |
| 2010/0185277 | A1 | 7/2010 | Braido |
| 2010/0191326 | A1 | 7/2010 | Alkhatib |
| 2010/0204781 | A1 | 8/2010 | Alkhatib |
| 2010/0204785 | A1 | 8/2010 | Alkhatib |
| 2010/0217382 | A1 | 8/2010 | Chau |
| 2010/0249911 | A1 | 9/2010 | Alkhatib |
| 2010/0249923 | A1 | 9/2010 | Alkhatib |
| 2010/0286768 | A1 | 11/2010 | Alkhatib |
| 2010/0298931 | A1 | 11/2010 | Quadri |
| 2011/0029072 | A1 | 2/2011 | Gabbay |
| 2011/0264207 | A1 | 10/2011 | Bonhoeffer |
| 2012/0215303 | A1* | 8/2012 | Quadri .................. A61F 2/2418 623/2.18 |
| 2013/0116779 | A1 | 5/2013 | Weber |

FOREIGN PATENT DOCUMENTS

| | | | |
|---|---|---|---|
| DE | 202008009610 | U1 | 12/2008 |
| EP | 0850607 | A1 | 7/1998 |
| EP | 1000590 | A1 | 5/2000 |
| EP | 1360942 | A1 | 11/2003 |
| EP | 1584306 | A1 | 10/2005 |
| EP | 1598031 | A2 | 11/2005 |
| EP | 1360942 | B1 | 12/2005 |
| FR | 2850008 | A1 | 7/2004 |
| FR | 2847800 | B1 | 10/2005 |
| JP | 2010517624 | A | 5/2010 |
| JP | 2011512948 | A | 4/2011 |
| WO | 9117720 | A1 | 11/1991 |
| WO | 9716133 | A1 | 5/1997 |
| WO | 9832412 | A2 | 7/1998 |
| WO | 9913801 | A1 | 3/1999 |
| WO | 2001028459 | A1 | 4/2001 |
| WO | 0149213 | A2 | 7/2001 |
| WO | 0156500 | A2 | 8/2001 |
| WO | 2001054625 | A1 | 8/2001 |
| WO | 2001076510 | A2 | 10/2001 |
| WO | 2002036048 | A1 | 5/2002 |
| WO | 0247575 | A2 | 6/2002 |
| WO | 2003047468 | A1 | 6/2003 |
| WO | 2006073626 | A2 | 7/2006 |
| WO | 2007071436 | A2 | 6/2007 |
| WO | 2008070797 | A2 | 6/2008 |
| WO | 2009042196 | A2 | 4/2009 |
| WO | 2010008548 | A2 | 1/2010 |
| WO | 2010008549 | A1 | 1/2010 |
| WO | 2010096176 | A1 | 8/2010 |
| WO | 2010098857 | A1 | 9/2010 |

OTHER PUBLICATIONS

Andersen HR, Knudsen LL, Hasenkam JM. Transluminal implantation of artificial heart valves. Description of a new expandable aortic valve and initial results with implantation by catheter technique in closed chest pigs. European heart Journal. May 1, 1992;13(5):704-8.

Andersen, Henning Rud, Transluminal Catheter Implanted Prosthetic Heart Valves, International Journal of Angiology 7:102-106 (1998).

Braido, et al., U.S. Appl. No. 29/375,243, filed Sep. 20, 2010, titled “Surgical Stent Assembly”.

International Search Report and Written Opinion for Application No. PCT/US2013/048409 dated Dec. 18, 2013, 15 pages.

Knudsen LL, Andersen HR, Hasenkam JM. Catheter-Implanted Prosthetic Heart Valves: Transluminal catheter Implantation of a new expandable artificial heart valve in the descending thoracic aorta in isolated vessels and closed chest pigs. The International Journal of Artificial Organs. May 1993; 16(5):253-62.

Moazami et al., “Transluminal Aortic Valve Placement: A Feasibility Study With a Newly designed Collapsible Aortic Valve.”, ASAIO Journal, (19960900), vol. 42, pp. M381-M385.

Quaden et al., “Percutaneous aortic valve replacement: resection before implantation”, European J. of Cardio-thoracic Surgery, vol. 27, Issue 5, pp. 836-840, May 2005.

U.S. Appl. No. 29/375,260, filed Sep. 20, 2010.

Zegdi, Rachid, MD, PhD et al., “Is It Reasonable to Treat All Calcified Stenotic Aortic Valves With a Valved Stent?” 579-584, J. of the American College of Cardiology, vol. 51. No. 5, Feb. 5, 2008.

* cited by examiner

VALVE ASSEMBLY FOR CRIMP PROFILE

CROSS-REFERENCE TO RELATED APPLICATIONS

This application is a continuation of U.S. patent application Ser. No. 18/050,266, filed Oct. 27, 2022, which is a continuation of U.S. patent application Ser. No. 16/297,060, now U.S. Pat. No. 11,660,186, filed Mar. 8, 2019, which is a divisional of U.S. patent application Ser. No. 14/882,669, filed Oct. 14, 2015, now U.S. Pat. No. 10,470,880, which is a continuation of U.S. patent application Ser. No. 13/788,696, filed Mar. 7, 2013, now U.S. Pat. No. 9,241,791, which claims the benefit of the filing date of U.S. Provisional Patent Application No. 61/666,174 filed Jun. 29, 2012, the disclosures of which are hereby incorporated herein by reference.

BACKGROUND OF THE INVENTION

The present invention relates to heart valve replacement and, in particular, to collapsible prosthetic heart valves. More particularly, the present invention relates to collapsible prosthetic heart valves having a smaller, more consistent diameter.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as the sheath covering the valve is withdrawn.

Despite the various improvements that have been made to the collapsible prosthetic heart valve delivery process, conventional delivery devices, systems, and methods suffer from some shortcomings. For example, in conventional prosthetic valves a cuff and leaflets are attached to the stent, interfering with the full collapsibility of the stent. The cuff and leaflets may include excess tissue material not necessary for function. This excess tissue material unduly increases the crimp profile of the valve assembly. It is believed that a large crimp profile may be partially responsible for vascular injury during delivery of prosthetic heart valves. Moreover, slack in the cuff and/or valve assembly reduces the chronic outward radial force, leading to inferior valve performance.

There therefore is a need for further improvements to the devices, systems, and methods for transcatheter delivery of collapsible prosthetic heart valves, and in particular, self-expanding prosthetic heart valves. Among other advantages, the present invention may address one or more of these needs.

SUMMARY OF THE INVENTION

A method of assembling a prosthetic heart valve may include providing a collapsible and expandable stent having an annulus section and an aortic section, the annulus section having a first annulus diameter in a relaxed condition and a second annulus diameter less than the first annulus diameter in a collapsed condition. A constraint may be applied to the stent to constrain the annulus section to a predetermined annulus diameter between the first annulus diameter and the second annulus diameter. At least one of a cuff or a plurality of leaflets may be assembled to the constrained annulus section to form a prosthetic heart valve and the constraint may be removed from the stent after the assembly step.

In some examples, the aortic section has a first aortic diameter in the relaxed condition and a second aortic diameter less than the first aortic diameter in the collapsed condition, and the step of applying the constraint constrains the aortic section to a predetermined aortic diameter between the first aortic diameter and the second aortic diameter.

The constraint may include a first suture tied to the annulus section of the stent to constrain the diameter of the annulus section to the predetermined annulus diameter and a second suture tied to the aortic section of the stent to constrain the diameter of the aortic section to the predetermined aortic diameter. The predetermined annulus diameter may be between about 85% and about 95% mm of the first annulus diameter. The constraint may include at least one drawstring to constrain the diameter of the annulus section. The at least one drawstring may include a first suture tied to the annulus section of the stent to constrain the diameter of the annulus section to the predetermined annulus diameter.

In some examples, the removing step may include cutting the first suture to release the annulus section to an unconstrained annulus diameter between the predetermined annulus diameter and the first annulus diameter. The constraint may include at least one ring disposed about a circumference of the stent to constrain the diameter of the stent. The constraint may also include a first ring disposed about the annulus section of the stent and a second ring disposed about the aortic section of the stent. The first ring and the second ring may be coupled together by a helical portion.

In some examples, further comprising rotating the constraint with respect to the stent to facilitate the assembling step. The constraint may include a cylindrical body having a proximal opening, a distal opening, a lumen defined between the proximal opening and the distal opening, and at least one window in the body configured and arranged to permit assembly of the prosthetic heart valve therethrough. The at least one window may include three triangular windows evenly spaced about the circumference of the constraint. The constraint may include a cone portion at the distal opening. Cutouts in the body may be spaced to facilitate assembly of the heart valve. The constraint may further include at least two rings and a plurality of angled struts coupled to the at least two rings, the plurality of angled struts outlining a plurality of triangles.

A method of assembling a prosthetic heart valve includes providing a collapsible and expandable stent having an annulus section and an aortic section, the annulus section having a first annulus diameter in a relaxed condition and second annulus diameter less than the first annulus diameter in a collapsed condition. The stent may be cooled to a temperature below a predetermined temperature at which the diameter of the annulus section decreases to a predetermined diameter between the first and second diameters. At least one of the cuff or a plurality of leaflets may be assembled to the cooled stent to form a prosthetic heart valve.

In some examples, the step of cooling the stent may include placing the stent within a cooled air box. The predetermined temperature may be below the Austenitic Finish temperature.

BRIEF DESCRIPTION OF THE DRAWINGS

Various embodiments of the present invention are described herein with reference to the drawings, wherein.

Various embodiments of the present invention will now be described with reference to the appended drawings. It is to be appreciated that these drawings depict only some embodiments of the invention and are therefore not to be considered limiting of its scope.

DETAILED DESCRIPTION OF THE INVENTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient.

Figure 1:
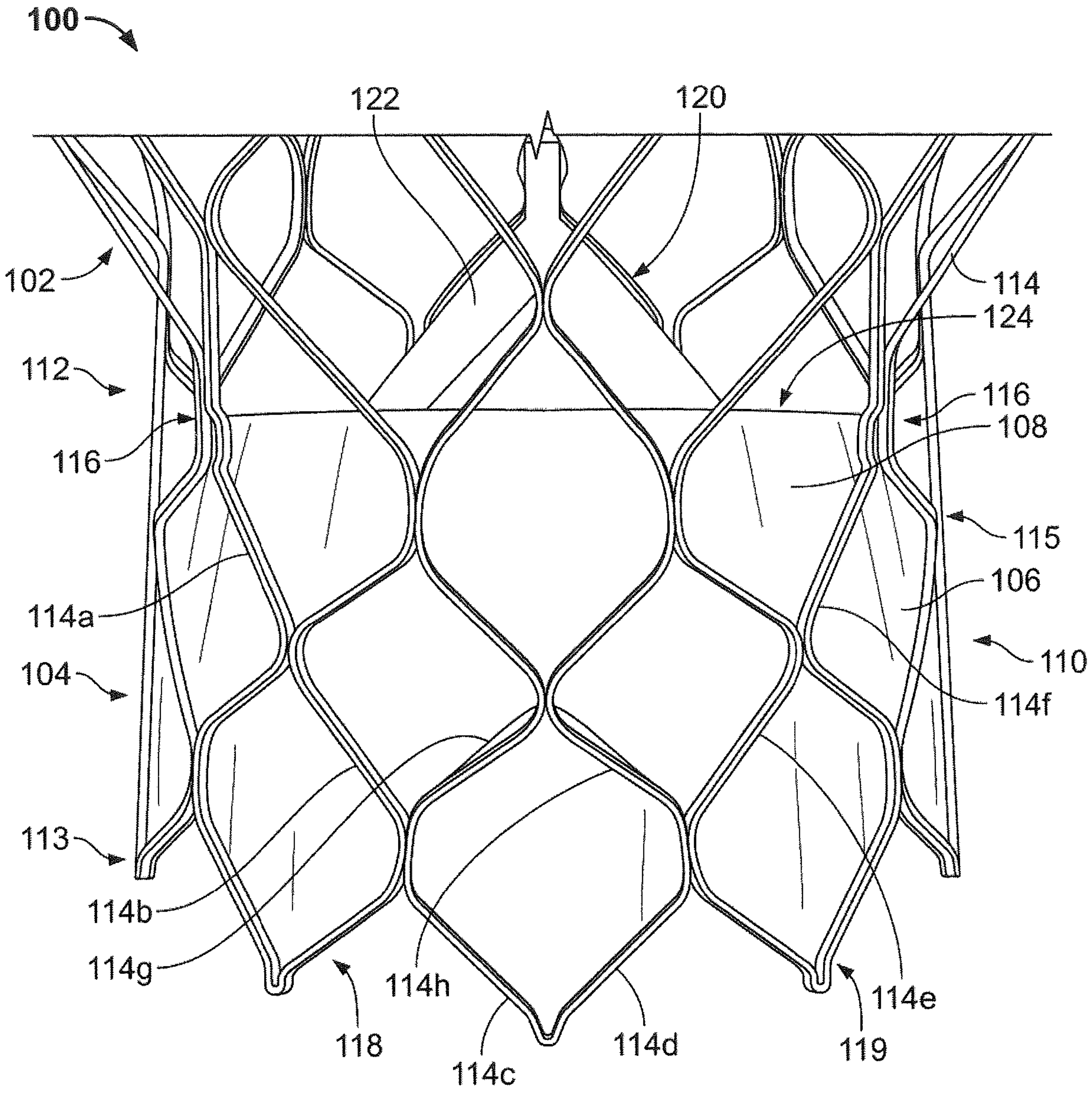
FIG. 1 is a partial side elevational view of a prosthetic heart valve including a stent and a valve assembly having a cuff and leaflets.

FIG. 1 shows a collapsible prosthetic heart valve 100 according to an embodiment of the present disclosure. The prosthetic heart valve 100 is designed to replace the function of a native aortic valve of a patient. Examples of collapsible prosthetic heart valves are described in International Patent Application Publication No. WO/2009/042196; U.S. Pat. Nos. 7,018,406; and 7,329,278, the disclosures of all of which are hereby incorporated herein by reference. As discussed in detail below, the prosthetic heart valve has an expanded condition and a collapsed condition. Although the invention is described herein as applied to a prosthetic heart valve for replacing a native aortic valve, the invention is not so limited, and may be applied to prosthetic valves for replacing other types of cardiac valves.

The prosthetic heart valve 100 includes a stent or frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. The stent 102 may have an annulus section 110, an aortic section 111 (FIG. 5A), and a transition section (not shown) disposed between the annulus and aortic sections. Each of the annulus section 110 and the aortic section 111 of the stent 102 includes a plurality of cells 112 connected to one another around the stent. The annulus section 110 and the aortic section 111 of the stent 102 may include one or more annular rows of cells 112 connected to one another. For instance, the annulus section 110 may have two annular rows of cells 112. When the prosthetic heart valve 100 is in the expanded condition, each cell 112 may be substantially diamond shaped. Regardless of its shape, each cell 112 is formed by a plurality of struts 114. For example, a cell 112 may be formed by four struts 114.

The stent 102 may include commissure features 116 connecting at least two cells 112 in the longitudinal direction of the stent 102. The purpose of the commissure features 116 will become apparent from the description below.

The prosthetic heart valve 100 also includes a valve assembly 104 attached inside the annulus section 110 of the stent 102. United States Patent Application Publication No. 2008/0228264, filed Mar. 12, 2007, and United States Patent Application Publication No. 2008/0147179, filed Dec. 19, 2007, the entire disclosures of both of which are hereby incorporated herein by reference, describe suitable valve assemblies. The valve assembly 104 may be wholly or partly formed of any suitable biological material, polymer, fabric or other suitable fiber. Examples of biological materials suitable for the valve assembly 104 include, but are not limited to, porcine or bovine pericardial tissue. Examples of polymers suitable for the valve assembly 104 include, but are not limited to, polyurethane, ultra-high-molecular-weight polyurethane and polyester.

The valve assembly 104 may include a cuff 106 disposed on the luminal surface of annulus section 110, on the abluminal surface of annulus section 110, or on both surfaces, and the cuff may cover all or part of either or both of the luminal and abluminal surfaces of the annulus section. The cuff and/or the sutures used to attach the valve assembly 104 to stent 102 may be formed from or include ultra-high-molecular-weight polyethylene. FIG. 1 shows cuff 106 disposed on the luminal surface of annulus section 110 so as to cover part of the annulus section while leaving other parts thereof uncovered. The cuff 106 may be attached to stent 102 by one or more strings or sutures passing through the cuff and around selected struts 114 of the stent. The valve assembly 104 may further include a plurality of leaflets 108 which collectively function as a one-way valve. A first edge 122 of each leaflet 108 may be attached to the stent 102 between two adjacent commissure features 116 by any suitable attachment means, such as suturing, stapling, adhesives or the like. For example, the first edge 122 of each leaflet 108 may be sutured to the stent 102 by passing strings or sutures through the cuff 106 of the valve assembly 104. The leaflets 108 may be attached to the stent 102 along at least some struts 114 of the stent and through the eyelets in the commissure features 116 to enhance the structural integrity of the valve assembly 104. A second or free edge 124 of each leaflet 108 may coapt with the corresponding free edges of the other leaflets, thereby enabling the leaflets to function collectively as a one-way valve.

As shown in FIG. 1, at least one leaflet 108 may be attached to the stent 102 so that its first edge 122 is disposed substantially along specific struts 114*a*, 114*b*, 114*c*, 114*d*, 114*e* and 114*f* located in the annulus section 110 of the stent. That is, the edge 122 is positioned in substantial alignment with struts 114*a*, 114*b*, 114*c*, 114*d*, 114*e*, and 114*f*. Struts 114*a*, 114*b*, and 114*c* may be connected to one another in substantially end-to-end fashion diagonally along three cells 112, beginning with an end of the strut 114*a* connected to a commissure feature 116 and ending with an end of strut 114*c* connected to an end of strut 114*d*. Struts 114*c* and 114*d* are part of the same cell 112 and may collectively define a substantially right angle between them. Struts 114*d*, 114*e*, and 114*f* may be connected to one another in substantially end-to-end fashion diagonally along three cells 112, beginning with an end of the strut 114*f* connected to a commissure feature 116 and ending with the connection between the end of strut 114*c* and the end of strut 114*d*.

As discussed above, the leaflets 108 may be attached directly to and supported by the struts 114*a*, 114*b*, 114*c*, 114*d*, 114*e*, and 114*f*, and by commissure features 116, such as by suturing. In such event, the cuff 106 may perform little or no supportive function for the leaflets 108. Hence, the cuff 106 is not subjected to high stresses and is therefore less likely to wear during use. In light of this, the thickness of the cuff may be reduced. Reducing the thickness of the cuff 106 results in a decrease in the volume of the valve assembly 104 in the collapsed condition (e.g., every mm of diameter is a 3 fold decrease in volume of cuff circumferentially and possible a smaller leaflet since it does not have to be as large to be assembled at a larger diameter). This decreased volume is desirable as it enables the prosthetic heart valve 100 to be implanted in a patient using a delivery device that is smaller in cross-section than conventional delivery devices. In addition, since the material forming the stent struts 114 is stronger than the material forming the cuff 106, the stent struts 114 may perform the supportive function for the leaflets 108 better than the cuff 106.

The volume of the valve assembly 104 may be further reduced by having the cuff 106 cover only a portion of the surface of annulus section 110. With continued reference to FIG. 1, the first or proximal end 118 of the cuff 106 may substantially follow the contour of the first or proximal end 119 of the stent 102. As such, the proximal end of the cuff 106 may have a generally sinusoidal or zigzag shape. This eliminates any free edge of the cuff 106, which otherwise might extend directly between the cusps of the cells 112 at the proximal end 119 of the stent 102, and enables the entire length of the proximal end 118 of the cuff 106 to be secured to the stent 102. The second or distal end 120 of the cuff 106, on the other hand, may be disposed substantially along at least some struts 114, but not necessarily the struts in a single annular row of cells 112. More particularly, the distal end 120 of the cuff 106 may follow the stent struts 114 up to the commissure features 116, such that the cuff covers all of the cells 112 in the bottom annular row 113 of cells and in a second annular row 115 of cells located between the commissure features and the proximal end 119 of the stent 102, but covers a lesser area of cells in the annular regions between the commissure features. In other words, the distal end 120 of the cuff 106 may be disposed substantially along struts 114*a*, 114*b*, 114*e*, 114*f*, 114*g* and 114*h*, as shown in FIG. 1. Strut 114*g* may be connected at one end to strut 114*h*, and at the other end to the intersection of struts 114*b* and 114*c*. Strut 114*h* may be connected at one end to strut 114*g*, and at the other end to the intersection of struts 114*d* and 114*e*. Struts 114*c*, 114*d*, 114*g*, and 114*h* collectively form a single cell 112.

As a result of the foregoing configuration, all of the cells 112 in the bottom annular row 113 of cells may be entirely covered by the cuff 106. The cuff 106 may also entirely cover those cells 112 in the second annular row 115 that are located directly below the commissure features 116. All of the other cells 112 in the stent 102 may be open or not covered by the cuff 106. Hence, there may be no cells 112 which are only partially covered by the cuff 106.

Since the edges of the valve leaflets 108 extend up to the second annular row 115 of cells 112 only in the regions of the commissure features 116, there is little to no likelihood of leakage in the area of the cells between the commissure features in the second annular row of cells, and therefore no need for the cuff 106 to cover this area. This reduction in the area of the cuff 106, both at the proximal end 118 and at the distal end 120 thereof, reduces the amount of material in the valve assembly 104, thereby enabling the prosthetic valve 100 to achieve a smaller cross-section in the collapsed condition.

In operation, the embodiments of the prosthetic heart valve described above may be used to replace a native heart valve, such as the aortic valve, a surgical heart valve or a heart valve that has undergone a surgical procedure. The prosthetic heart valve may be delivered to the desired site (e.g., near a native aortic annulus) using any suitable delivery device, including the delivery device described in detail below. During delivery, the prosthetic heart valve is disposed inside the delivery device in the collapsed condition. The delivery device may be introduced into a patient using a transfemoral, transapical or transseptal approach. Once the delivery device has reached the target site, the user may deploy the prosthetic heart valve described above. Upon deployment, the prosthetic heart valve expands into secure engagement within the native aortic annulus. When the prosthetic heart valve is properly positioned inside the heart, it works as a one-way valve, allowing blood to flow in one direction and preventing blood from flowing in the opposite direction.

As previously discussed, a large valve diameter will lead to a large crimp profile and possible vascular injury during implantation of the prosthetic heart valve. One way to reduce the valve crimp profile is to eliminate unneeded tissue from the valve. Since the diameter of the valve when fully deployed and operating within the native valve annulus of the patient is typically smaller than the fully expanded diameter of the valve when built, excess valve tissue will typically be present when the valve is built using conventional techniques.

The following describes new methods and devices for pre-assembling or building a prosthetic heart valve at a smaller, constrained diameter to reduce this excess valve tissue. By building the heart valve at a constrained diameter, less tissue is used. When the constraint is removed, the valve does not expand to the fully expanded diameter of the stent, but rather expands to an intermediate diameter based on the amount of tissue used. This intermediate diameter is larger than the diameter of the native valve annulus so that a sufficient outward radial force is exerted on the valve annulus to hold the valve in place, but is closer to the size of the native valve annulus than the fully expanded diameter of the stent. Moreover, by building the heart valve at a constrained diameter, less material is used, allowing for a reduced crimp profile. In addition, building the prosthetic heart valve using these methods produces a more consistent valve diameter.

Figure 2:
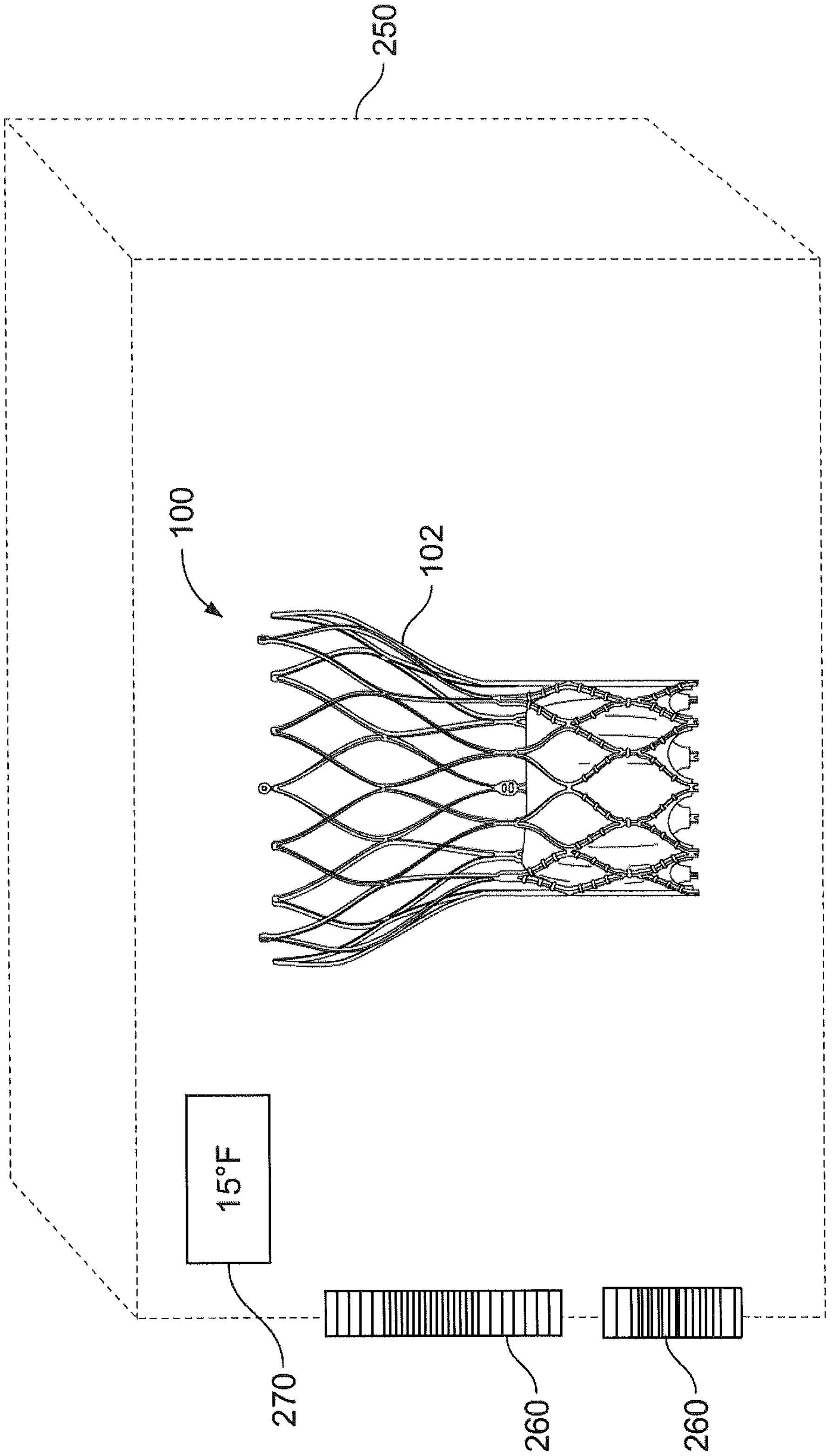
FIG. 2 is schematic perspective view of a prosthetic heart valve in a cooled air box.

FIG. 2 illustrates one method of building the prosthetic heart valve without physically constraining the valve. The stent 102 of the prosthetic heart valve 100 may be formed of a shape-memory material, such as nitinol, having properties that are dependent on the temperature of the material. As a result, the shape of stent 102 is temperature dependent. Prosthetic heart valve 100 may be built inside a cooled air box 250, the temperature and/or humidity of which may be displayed on display 270 and adjusted using dials 260. The desired temperature within cooled air box 250 may be chosen based on the material of stent 102. For example, cooled air box 250 may allow a user or technician to assemble a prosthetic heart valve 100 below room temperature. In some examples, heart valve 100 may be assembled in a cooled air box 250 at a temperature below the Austenite Finish temperature. In at least some examples, assembly is performed at a temperature of between 18 and 22° C. Due to this cold temperature, stent 102 may assume a diameter during assembly that is smaller than its diameter at room temperature. After assembly, the stent 102 is removed from cooled air box 250 and, as the stent gradually returns back towards its austenite finish transition temperature, it will return to the intended heat-set shape. However, the tissue assembled to the stent 102 may constrain this expansion, and the assembled valve may only expand to an intermediate diameter. Alternatively, heart valve 100 may be built via dipping in hot or cold saline to set the shape, then assembling at room temperature.

Figure 3:
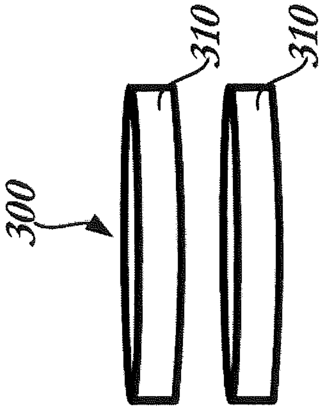
FIG. 3 is a side perspective view of a fixation device having two rings.

Instead of using cooled air box 250, the prosthetic heart valve 100 may be physically constrained prior to and during assembly so that less tissue or material is used to form the valve. FIG. 3 illustrates a fixation device 300, which includes a pair of rings 310 that may be used to constrain the valve. Each ring 310 may be made of suitable synthetic polymers including, but not limited to, thermoplastics, such as polyolefins, polyesters, polyamides, polysulfones, acrylics, polyacrylonitriles, polyetheretherketone (PEEK), and polyaramides. For example, rings 310 may be formed of silicone.

Prior to attaching the leaflets 108 or the cuff 106, rings 310 may be placed over the stent 102 to constrain the stent to a first diameter that is less than the fully expanded diameter. The fully expanded diameter, for example, on a valve labeled "29 mm" may be slightly higher than 29 mm, (e.g., 29-30 mm). The use range of this valve may be in the range of about 25 mm to 27 mm so as to have 2-4 mm of interference with the anatomy to have enough radial force to stay in place. The build diameter may be selected between the stent parent diameter and the high use range (e.g., 25-30 mm in this case). The build diameter may vary for each valve size. Thus, rings 310 may constrain the stent 102, for example, to a diameter of between about 85% and about 95% of the fully expanded diameter.

Two rings 310 may be used to constrain the stent 102, one at the annulus section 110 and another at the aortic section 111. The rings 310 may also be disposed near the commissure features 116 or anywhere on the stent as desired. It will be understood that a single ring 310 or multiple rings such as three, four or five rings may be used to constrain the stent. Rings 310 may be slid up or down the stent 102 to allow the user or technician to couple the leaflets 108 and/or cuff 106 to the stent, such as by sewing. Rings 310 may also be slid out of the way to clip or remove excess tissue or material from the cuff 106, the leaflets 108 or both.

Figure 4B:
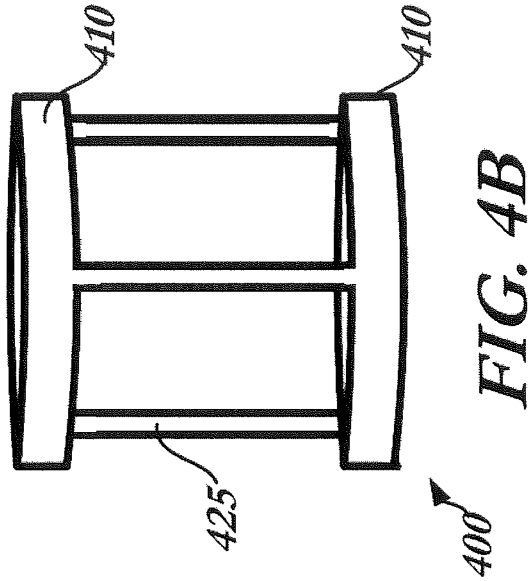
FIGS. 4A and 4B are side perspective views of fixation devices having two rings coupled to a helical portion.
Figure 4A:
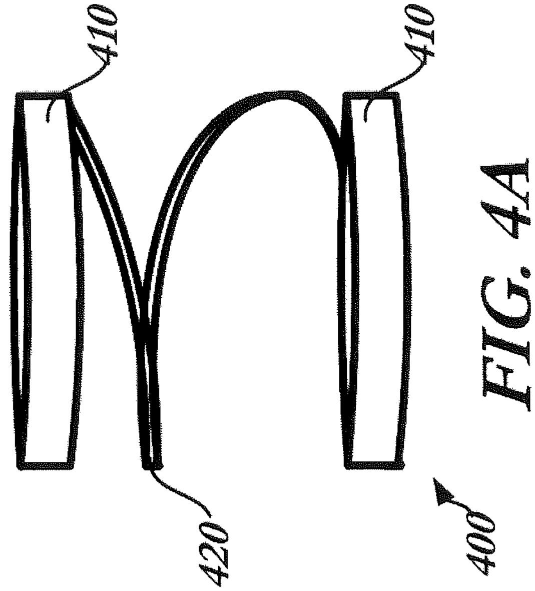

FIG. 4A illustrates a fixation device 400 for aiding in the assembly of a prosthetic heart valve in accordance with another embodiment of the invention. Fixation device 400 includes a pair of rings 410 joined to one another by a helical portion 420. The rings 410 may be disposed around the annulus section 110 and aortic section 111 of a stent 102. Because the two rings 410 are connected, fixation device 400 may be better secured to the stent during assembly. If helical portion 420 impedes assembly of the valve, fixation device 400 may be simply rotated around the stent 102 to better allow the user to see the valve, attach tissue or material to the stent, or trim excess material from the cuff (if necessary). In this manner, fixation device 400 may be gradually rotated around the stent 102 as the operator assembles the leaflets 108 or the cuff 106 to the stent. In another example, shown in FIG. 4B, fixation device 400 includes a pair of rings 410 joined to one another by three connecting struts 425. It will be understood that rings 410 may be joined by one, two, three, four, five or more struts 425.

Figure 5B:
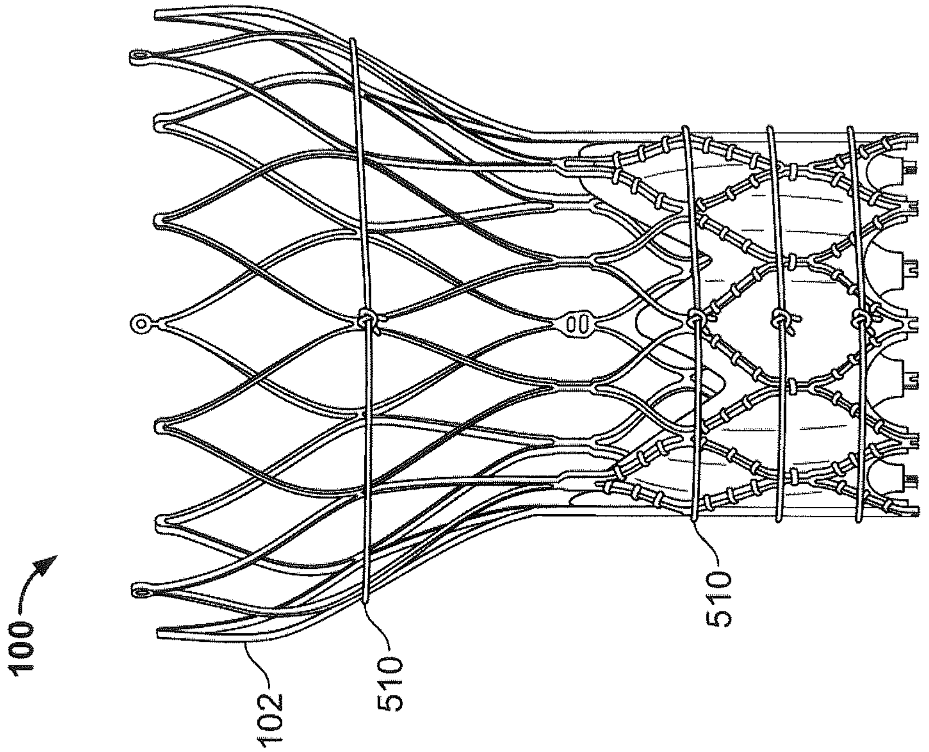
FIG. 5B is a side perspective view of a prosthetic heart valve constrained with drawstrings at the annulus section and the aortic section.
Figure 5A:
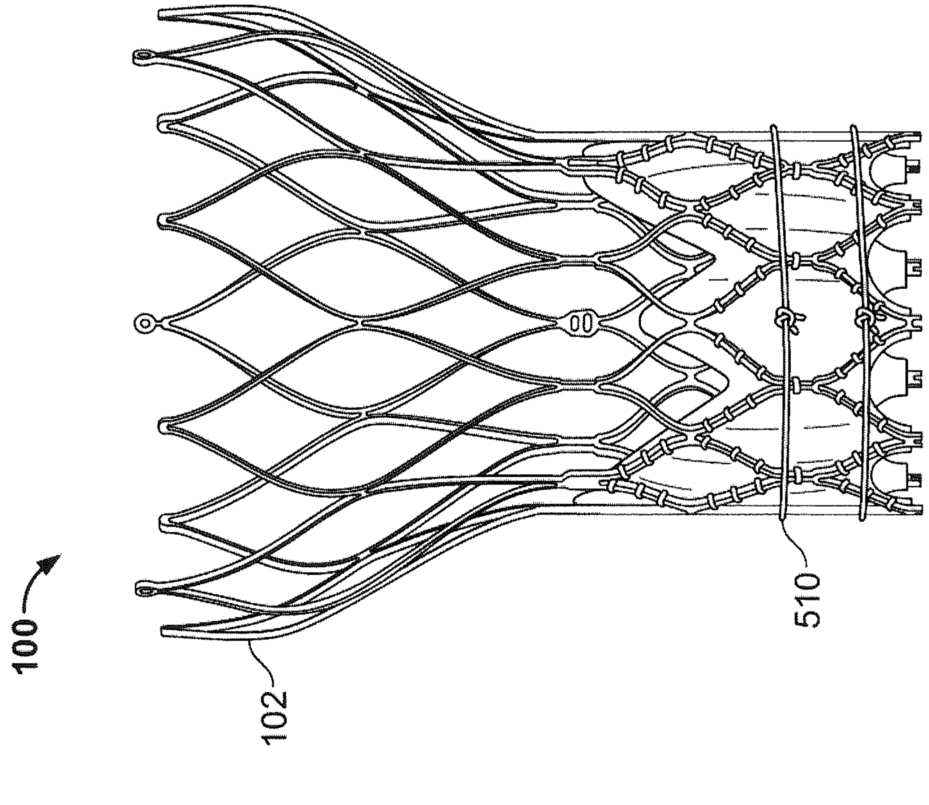
FIG. 5A is a side perspective view of a prosthetic heart valve constrained with drawstrings at the annulus section.

FIGS. 5A and 5B illustrate methods of constraining the prosthetic heart valve 100 using drawstrings 510. Drawstrings 510 may be formed of sutures or straps that tie around a portion of the stent 102 during assembly. As seen in FIG. 5A, a pair of drawstrings 510 may be tied around the annulus section 110 of the stent 102 during assembly. The drawstrings 510 may act to constrain the stent to a desired diameter until assembly has been completed. After assembly of the prosthetic heart valve 100, the drawstrings may be severed and removed. FIG. 5B illustrates a similar example of constraining the prosthetic heart valve 100 using drawstrings 510. The example of FIG. 5B utilizes three drawstrings 510 at the annulus section 110 of stent 102 and a fourth drawstring 510 near the aortic section 111. It will be understood that any number of drawstrings 510 may be used as desired to constrain the heart valve 100 during assembly. Moreover, it will be understood that the drawstrings may be tied around any portion of the stent 102, including the annulus section 110, transition section, aortic section 111 and/or the commissure features 116 (if any), and may be tied around or weaved through any portion of the stent such as, for example, the struts 114.

Figure 6:
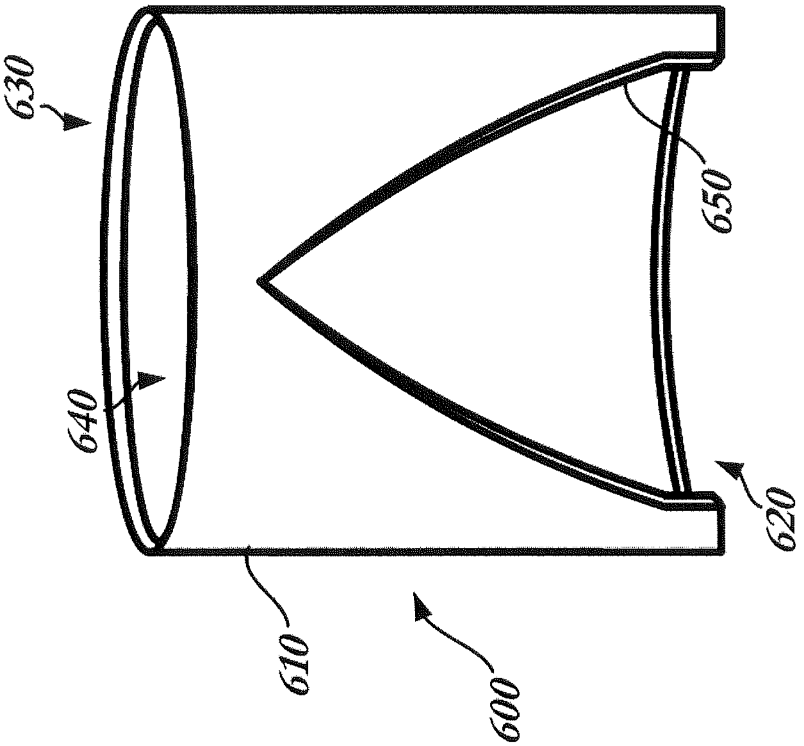
FIG. 6 is a side perspective view of a fixation device having a cylindrical body and a substantially triangular window.

FIG. 6 illustrates a fixation device 600 for facilitating the assembly of a prosthetic heart valve in accordance with a further embodiment of the invention. Fixation device 600 may include a generally cylindrical body 610 having a proximal opening 620, a distal opening 630 and a lumen 640 extending between the proximal and distal openings. Body 610 may be provided with a large window 650 extending from proximal opening 620 toward distal opening 630. Window 650 may have a relatively large width at the proximal opening 620, and may gradually narrow toward the distal opening 630 so as to define a generally triangular shape.

The lumen 640 through body 610 may be sized to receive a valve support stent 102. Specifically, stent 102 may be placed within the lumen 640 of fixation device 600 to constrain it to a first diameter during assembly of prosthetic valve 100. With stent 102 assembled in fixation device 600, window 650 provides access to the stent to enable the operator to sew, or otherwise assemble the valve leaflets 108 and/or cuff 106 thereto. Access to different regions on the circumference of stent 102 may be had simply by rotating the stent within fixation device 600 until the desired region is aligned with window 650. Alternatively, body 610 may include multiple windows 650 around its circumference. The windows 650 may be spaced equally or unequally around the circumference of body 610, as desired, in order to provide access to different regions of stent 102 needed to complete the assembly process. Moreover, windows 650 need not be generally triangular, but may be of any shape or size, such as circular, ovoid, rectangular, square or any other suitable shape. Where fixation device 600 includes multiple windows 650, the size and shape of the windows may all be the same, some may be the same, or they may all be different from one another.

Figure 7:
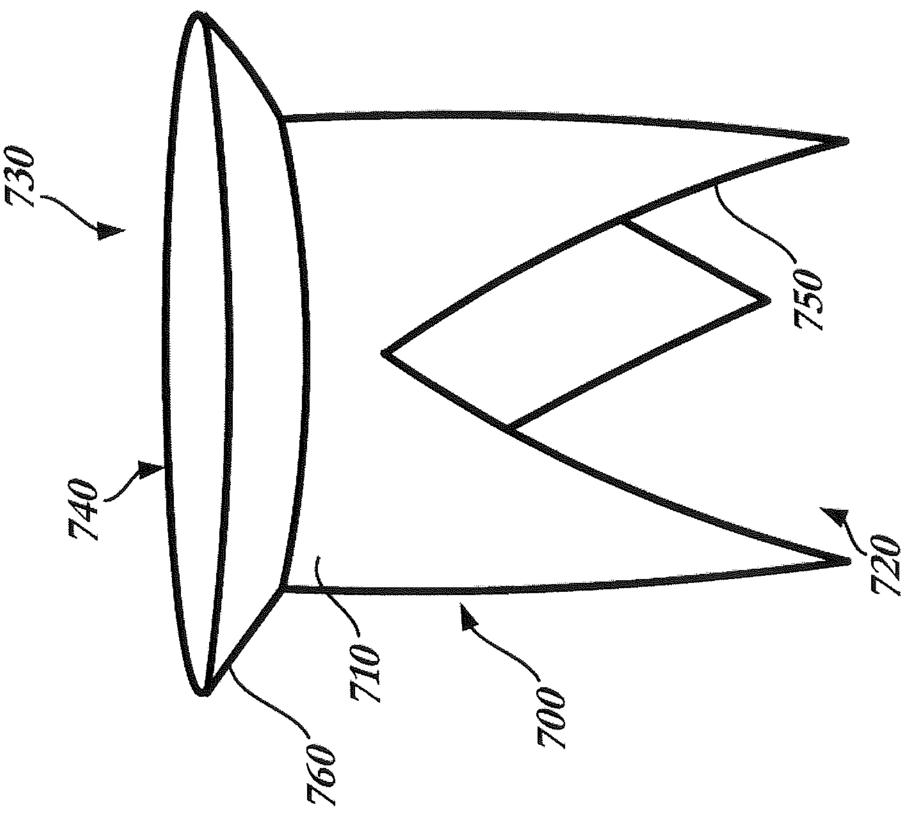
FIG. 7 is a side perspective view of a fixation device having a body, a cone portion and multiple windows.

FIG. 7 illustrates a variation of fixation device 600. Similar to fixation device 600, fixation device 700 may include a generally cylindrical body 710 having a proximal opening 720, a distal opening 730 and a lumen 740 extending between the proximal and distal openings. The lumen 740 may be sized to receive a stent 102. Specifically, stent 102 may be placed within the lumen 740 of fixation device 700 to constrain it to a first diameter during assembly of prosthetic valve 100. Body 710 may have three triangular windows 750 disposed 120° apart. An additional cone portion 760 may be provided adjacent the distal opening 730 of body 710. The tapered walls of cone portion 760 may facilitate the loading of a stent 102 into lumen 740. Additionally, cone portion 760 may be sized to allow the aortic section 111 of stent 102 to be seated within it during assembly.

Figure 8:
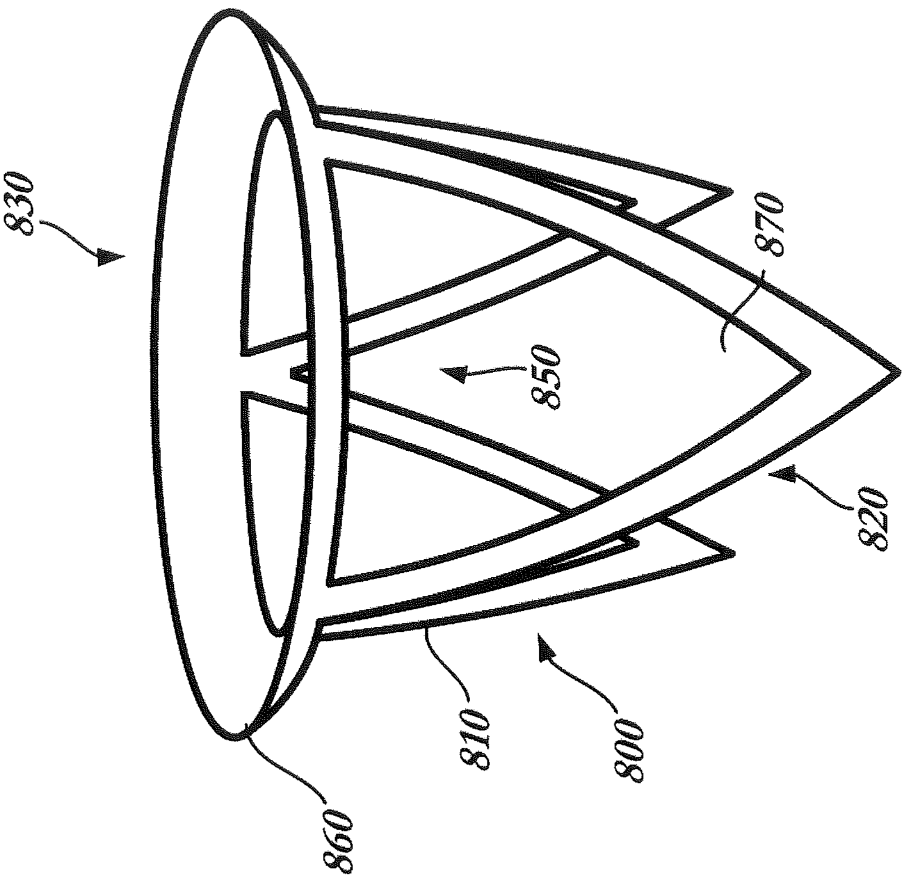
FIG. 8 is a side perspective view of a fixation device having a body with internal cutouts, and multiple windows.

In another variation, shown in FIG. 8, a fixation device 800 is similar to fixation device 700 with one primary difference. Rather than having solid wall structures between adjacent windows 850, as is the case in fixation device 700, the body 810 of fixation device 800 includes internal cutouts 870 between windows 850 to provide greater access to stent 102 to enable the operator to sew or otherwise attach the valve leaflets 108 and/or cuff 106 thereto. The resulting fixation device 800 includes a cone portion 860 and a body 810 formed by a plurality of strut members joined to the cone portion to form triangular shapes. It will be understood that rather than a cone portion 860, fixation device 800 may include a conventional ring.

Figure 9:
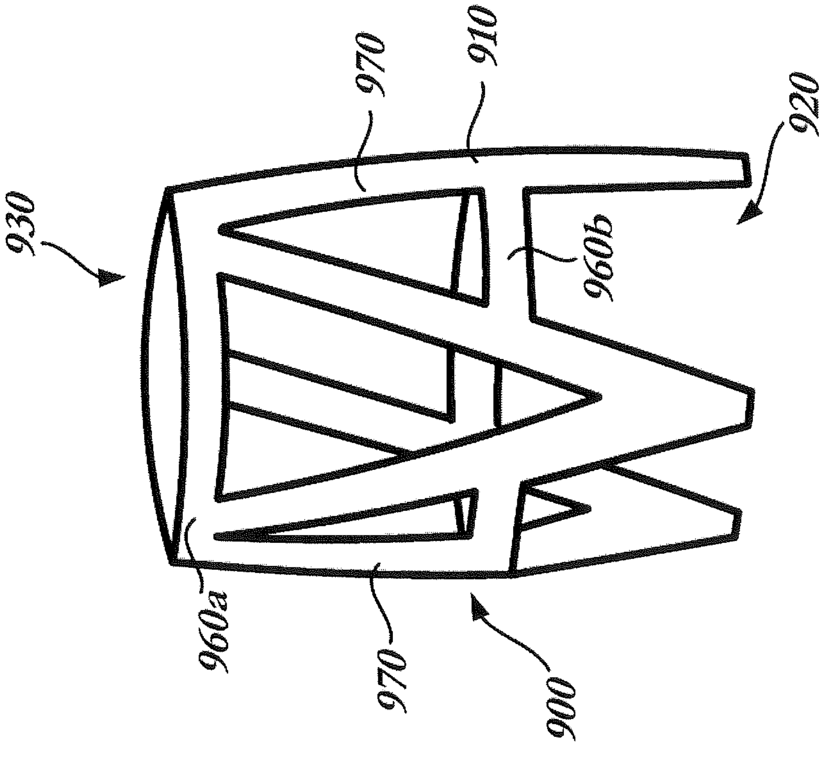
FIG. 9 is a side perspective view of a fixation device having a pair of rings and angled struts.

Another fixation device 900 in accordance with the present invention is illustrated in FIG. 9. Fixation device 900 includes a body 910 having a proximal opening 920, a distal opening 930 and a lumen extending between the proximal and distal openings. Body 910 may include horizontal struts forming a top ring 960*a* adjacent the distal open end 930, which corresponds to the aortic section 111 of stent 102, and horizontal struts forming an intermediate ring 960*b* intermediate the proximal and distal openings, which corresponds to the transition section or annulus section of the stent. Intermediate ring 960*b* may be continuous or discontinuous as seen in FIG. 9, and may be used to align the prosthetic heart valve 100 within fixation device 900, such as by aligning the commissure features 116 of the valve with portions of the intermediate ring. Fixation device 900 may be formed with any desirable distance between rings 960*a* and 960*b*. Joined to rings 960*a*, 960*b* are a plurality of angled struts 970. With the exception of intermediate ring 960*b*, body 910 and angled struts 970 may be formed similar to body 810 such that angled struts 970 essentially form three inverted triangles disposed around the circumference of fixation device 900.

Figure 10:
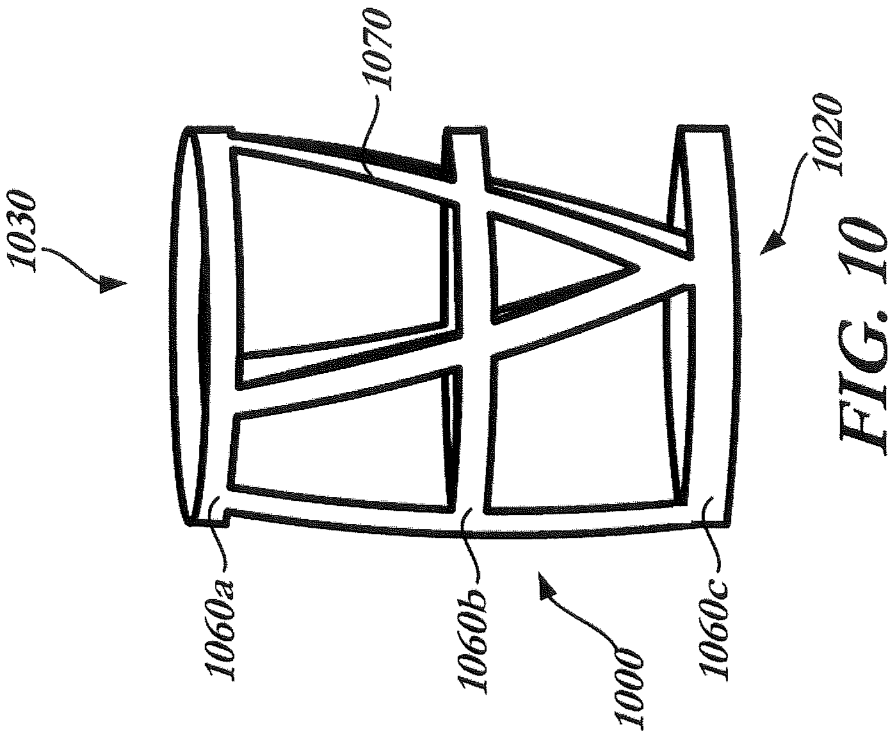
FIG. 10 is a side perspective view of a fixation device having three rings and angled struts.

FIG. 10 illustrates a fixation device 1000 similar the fixation device 900 of FIG. 9. Fixation device 1000 includes a body 1010 having a proximal opening 1020, a distal opening 1030 and a lumen extending between the proximal and distal openings. Body 1010 may include three rings, including a top ring 1060*a* corresponding to the aortic section 111 of a constrained stent 102, an intermediate ring 1060*b* corresponding to the transition section of a constrained stent and a bottom ring 1060*c* corresponding to the annulus section 110. It will be understood that fixation device 1000 may be formed with any desired spacing between the three rings 1060. Joined to rings 1060 are a plurality of angled struts 1070, similar to those shown in the examples above.

Using the cooled air box 250 or any of the fixation devices described above, a user or operator is able to assemble a prosthetic heart valve at a diameter that is smaller than the fully expanded diameter of stent 102. When the assembled valve is removed from the cooled air box or the fixation device, it does not expand to the fully expanded diameter of the stent, but rather expands to an intermediate diameter based on the amount of tissue used. This intermediate diameter allows less material to be used for the cuff and leaflets of the valve, enabling the valve to be crimped to a smaller profile, thereby facilitating its introduction into and deployment in a patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, features of the drawstring examples may be combined with a fixation device into a single embodiment. Moreover, a cooled air box may be used to assemble a prosthetic heart valve according to any of the preceding examples. Additionally, the constraint may be useful for assembling or constructing not only heart valves, such as transcatheter aortic valve implants, but also surgical valves, annuloplasty rings and the like. See above comments on diameters. It should also be noted in embodiments including constraints having rings that the top and bottom rings need not be of the same diameter. Moreover, while certain embodiments have been described using the word "ring," it will be understood that the term "ring" is not limited to a closed shape and that C-shaped configurations are also contemplated, for example. It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A system, comprising:

a prosthetic heart valve having a collapsible and expandable stent having an annulus section, the annulus section having a first annulus diameter in a relaxed condition and a second annulus diameter less than the first annulus diameter in a collapsed condition, the prosthetic heart valve further including a plurality of leaflets and a cuff; and a fixation device defining a fixation diameter that is greater than the second annulus diameter, and less than the first annulus diameter, the fixation device being removably coupleable to the prosthetic heart valve and configured and arranged to (i) constrain the annulus section, during assembly of at least one of the plurality of leaflets and the cuff, to an annulus diameter between the first annulus diameter and the second annulus diameter, and (ii) be removed from the prosthetic heart valve prior to loading within a delivery device.

2. The system of claim 1, wherein the stent further includes an aortic section having a first aortic diameter in the relaxed condition and a second aortic diameter less than the first aortic diameter in the collapsed condition, and wherein the fixation device further constrains the aortic section to an aortic diameter between the first aortic diameter and the second aortic diameter.

3. The system of claim 1, wherein the fixation diameter is between about 85% and about 95% of the first annulus diameter.

4. The system of claim 1, wherein the fixation device comprises at least one ring.

5. The system of claim 4, wherein the at least one ring is configured to be disposed about a circumference of the stent.

6. The system of claim 4, wherein the at least one ring is part of a cylindrical body, having a proximal opening, a distal opening and a lumen defined between the proximal opening and the distal opening, and at least one window in the cylindrical body configured and arranged to permit assembly of the prosthetic heart valve therethrough.

7. The system of claim 2, wherein the fixation device comprises a first ring disposed about the annulus section of the stent and a second ring disposed about the aortic section of the stent.

8. The system of claim 7, wherein the first ring and the second ring are coupled together by a linear portion.

9. The system of claim 7, wherein the first ring and the second ring are spaced from one another.

10. The system of claim 1, wherein the fixation device is rotatable with respect to the stent to facilitate assembly of a leaflet to the stent.

11. The system of claim 1, wherein the fixation device comprises at least one suture.

12. The system of claim 11, wherein the fixation device comprises one suture.

13. The system of claim 11, wherein the fixation device comprises multiple sutures spaced from one another.

14. The system of claim 1, wherein the fixation device is continuous about the fixation diameter.

15. The system of claim 1, wherein the fixation device is discontinuous about the fixation diameter.

16. The system of claim 1, wherein the fixation device is C-shaped.

17. A system, comprising:

a prosthetic heart valve having a collapsible and expandable stent having an annulus section, the annulus section having a first annulus diameter in a relaxed condition and a second annulus diameter less than the first annulus diameter in a collapsed condition, the prosthetic heart valve further including a plurality of leaflets and a cuff; and a fixation device defining a fixation diameter that is greater than the second annulus diameter, and less than the first annulus diameter, the fixation device being removably coupleable to the collapsible and expandable stent and configured and arranged to (i) constrain, during assembly of at least one of the plurality of leaflets and the cuff, the annulus section of the collapsible and expandable stent to an annulus diameter between the first annulus diameter and the second annulus diameter, and (ii) be removed from the prosthetic heart valve prior to loading within a delivery device.

18. The system of claim 17, wherein the fixation device comprises at least one ring.

19. The system of claim 18, wherein the at least one ring is configured to be disposed about a circumference of the stent.

20. The system of claim 18, wherein the at least one ring comprises a first ring disposed about the annulus section of the stent and a second ring disposed about an aortic section of the stent.

* * * * *